US010925633B2

(12) United States Patent
Page et al.

(10) Patent No.: US 10,925,633 B2
(45) Date of Patent: Feb. 23, 2021

(54) NEEDLE GUIDE DEVICE AND METHOD

(71) Applicant: The Research Foundation for The State University of New York, Albany, NY (US)

(72) Inventors: Christopher Page, Rye Brook, NY (US); Anurag Purwar, Dix Hills, NY (US); Pranav Korrapati, Stony Brook, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 438 days.

(21) Appl. No.: 15/574,169

(22) PCT Filed: May 12, 2016

(86) PCT No.: PCT/US2016/031965
§ 371 (c)(1),
(2) Date: Nov. 15, 2017

(87) PCT Pub. No.: WO2016/186937
PCT Pub. Date: Nov. 24, 2016

(65) Prior Publication Data
US 2018/0125528 A1     May 10, 2018

Related U.S. Application Data

(60) Provisional application No. 62/162,119, filed on May 15, 2015.

(51) Int. Cl.
*A61B 90/11*     (2016.01)
*A61B 17/34*     (2006.01)
(Continued)

(52) U.S. Cl.
CPC .......... *A61B 17/3403* (2013.01); *A61B 17/34* (2013.01); *A61B 90/11* (2016.02);
(Continued)

(58) Field of Classification Search
CPC ......... A61B 90/10; A61B 90/11; A61B 90/13; A61B 2090/101; A61B 2090/103;
(Continued)

(56) References Cited

U.S. PATENT DOCUMENTS 3,021,842 A * 2/1962 Flood .................. A61M 5/3287
                                                     604/175
4,809,694 A * 3/1989 Ferrara .............. A61B 17/3403
                                                     606/130
(Continued)

FOREIGN PATENT DOCUMENTS

| EP | 2 042 114 A1 | 4/2009 |
|----|--------------|--------|
| WO | 02/13714 A1 | 2/2002 |
| WO | 02/30352 A2 | 4/2002 |

OTHER PUBLICATIONS

International Search Report and Written Opinion dated Aug. 19, 2016 issued in PCT/US2016/031965.
(Continued)

*Primary Examiner* — Diane D Yabut
*Assistant Examiner* — Christian D Knauss
(74) *Attorney, Agent, or Firm* — Scully, Scott, Murphy & Presser, P.C.

(57) ABSTRACT

The present disclosure provides a fluoroscopic needle guide device for use in medical procedures that facilitate the direct targeting of a pre-identified target in a subject and methods for reaching the same with a medical device. The present disclosure includes fluoroscopic needle guide devices including detachable alignment indicators and methods for using the same.

15 Claims, 13 Drawing Sheets

(51) Int. Cl.
*A61M 5/158* (2006.01)
*A61B 90/00* (2016.01)

(52) U.S. Cl.
CPC ..... *A61M 5/158* (2013.01); *A61B 2017/3407* (2013.01); *A61B 2090/0811* (2016.02); *A61B 2090/3966* (2016.02)

(58) Field of Classification Search
CPC ........ A61B 17/3403; A61B 2017/3405; A61B 2017/3407; A61B 2017/3409; A61B 34/20; A61M 5/158; A61M 2005/1586
See application file for complete search history.

(56) References Cited

U.S. PATENT DOCUMENTS

| | | | |
|---|---|---|---|
| 5,367,781 A | | 11/1994 | Hsu |
| 5,375,588 A | * | 12/1994 | Yoon ................. A61B 17/3403 600/114 |
| 5,405,330 A | | 4/1995 | Zunitch et al. |
| 6,267,769 B1 | * | 7/2001 | Truwit ................. A61B 90/11 606/1 |
| 6,527,782 B2 | * | 3/2003 | Hogg ................. A61B 17/3417 128/899 |
| 6,689,142 B1 | * | 2/2004 | Tremaglio, Jr. ... A61B 17/3403 604/114 |
| 8,057,487 B2 | | 11/2011 | Chu et al. |
| 2002/0049451 A1 | * | 4/2002 | Parmer ................. A61B 90/11 606/108 |
| 2004/0260312 A1 | | 12/2004 | Magnusson et al. |
| 2013/0096570 A1 | * | 4/2013 | Solar ................. A61B 17/00234 606/108 |
| 2013/0267834 A1 | * | 10/2013 | McGee ................. A61M 5/427 600/424 |
| 2014/0276416 A1 | * | 9/2014 | Nelson ................. A61M 25/02 604/151 |
| 2014/0276559 A1 | | 9/2014 | Page |
| 2014/0288578 A1 | | 9/2014 | Solar et al. |
| 2015/0057570 A1 | * | 2/2015 | Chin ................. A61B 10/0283 600/566 |

OTHER PUBLICATIONS

Extended Supplementary European Search Report dated Nov. 30, 2018 in European Patent Application No. 16 79 6966.6.
SeeStar® Guiding Device-Optimize Efficiency During Your Procedures With SeeStar®, AprioMed (2 pages) (2010).
Simplify-Needle Holder for Image Guided Interventions—-NeoRad (2 pages) (2018).

* cited by examiner

FIG. 9
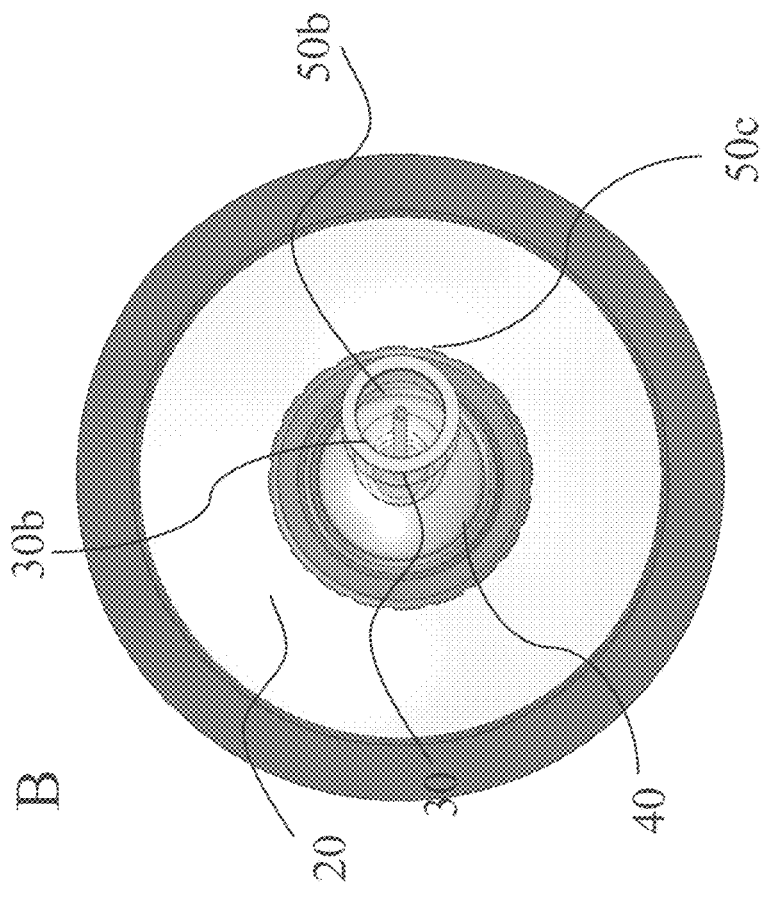
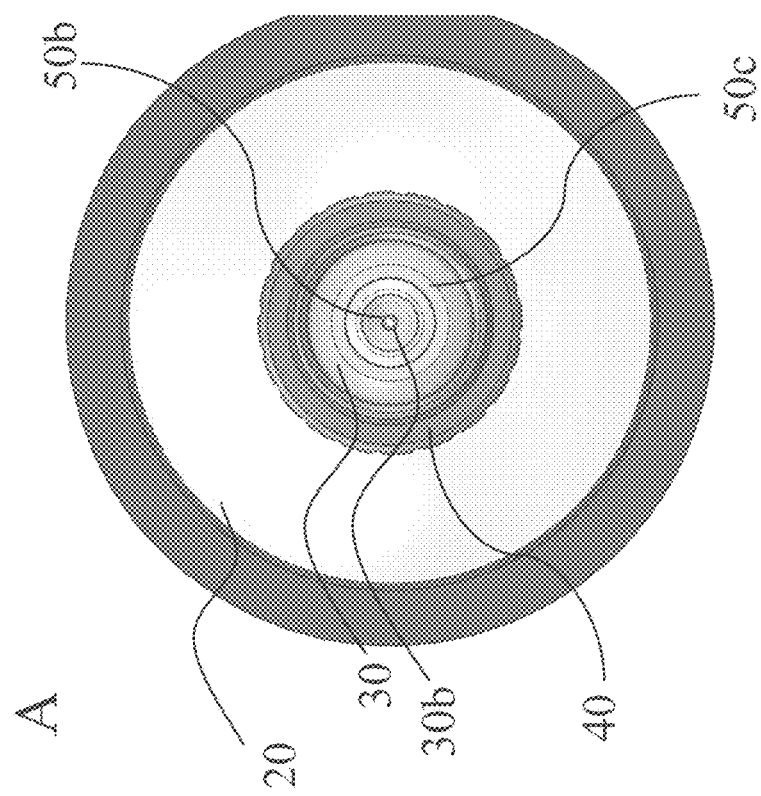

NEEDLE GUIDE DEVICE AND METHOD

CROSS REFERENCE TO RELATED APPLICATION

The present application is a 371 of International Application having Serial No. PCT/US2016/031965 filed on May 12, 2016, which claims benefit of U.S. Provisional Application No. 62/162,119 filed on May 15, 2015, the entire contents of which are incorporated herein by reference.

FIELD OF THE DISCLOSURE

The present disclosure relates to devices and methods for positioning and aligning medical devices during medical procedures. The instant disclosure further relates to fluoroscopic needle guides, which can be applied to the outer surface of a subject during a medical procedure to provide a user with a needle path that maintains a desired needle trajectory into the subject throughout the procedure.

BACKGROUND

Fluoroscopy is a medical imaging modality that displays a continuous X-ray image on a display (e.g., monitor), in which X-rays are emitted to a patient and the resulting image is relayed to the display showing movement or location of a particular part of the patients body (e.g., bone) or any instrument inserted therein, such as a needle or prosthesis.

Fluoroscopy can be used for the real-time guidance of needles or other medical devices into the body of a subject. For example, positioning of a needle is typically determined by manually aligning the needle parallel to the incident angle of an X-ray beam, which requires a user to repeatedly take X-ray images throughout the duration of the alignment process. The current methods and devices for the real-time guidance of needles have many drawbacks.

In such procedures, it is important that the position of the needle in a first plane (e.g., X plane) is maintained while the position of the needle is aligned or moved in a different plane (e.g., Y plane). Using current methods and devices such alignment requires multiple X-rays in both planes in order to accurately determine needle positioning at each point in the alignment process. Repeated exposure to X-ray emissions can have harmful side-effects for both the subject and practitioner, and thus should be limited or avoided altogether. Additionally, existing methods and devices require that the needle or device be completely withdrawn from the subject, re-positioned and re-inserted into the subject in order to slightly alter the alignment of the needle or adjust the needle path to reach a target location within the subject. Accordingly, existing alignment procedures result in numerous painful insertions of the needle or device during the duration of the procedure.

In view of the foregoing, medical instrument positioning systems and methods for using the same, which limit a subject's exposure to X-ray emissions and permit the user to adjust the path of a needle or device prior to insertion into a subject and maintain the desired trajectory path toward a target.

SUMMARY OF THE DISCLOSURE

The present disclosure provides a fluoroscopic needle guide device for use in medical procedures whereby a user, such as a radiologist, clinician or technician, must accurately traverse the tissue of a subject with a medical device, e.g., needle, such that the medical device reaches a precise target within the subject.

One aspect of the present disclosure includes a fluoroscopic needle guide device that includes an adhesive layer, a base member on the adhesive layer having a threaded portion surrounding an opening, a rotatable sphere seated on the opening in the base member, and a detachable threaded ring overlying a top portion of the rotatable sphere, whereby the detachable threaded ring interlocks with a threaded portion of the base and has an opening that overlies the outer surface of the rotatable sphere.

In an one embodiment of the present disclosure, the upper portion of the base member extends vertically above the bottom portion of base member and includes: an elongated opening that enables compression or expansion of the upper portion of the base member, a circular opening in a top surface of the base member, and a contact ring surrounding the circular opening that contacts the outer surface of a rotatable sphere when the rotatable ball is seated in the opening of the base member. The upper portion of the base member also includes a threaded opening (e.g. nut) for which a screw element can be affixed and used increase the friction between the rotatable ball and the contact ring.

In specific embodiments of the present disclosure the fluoroscopic needle guide device includes a detachable alignment indicator having a radio-opaque inner shaft and a cone shaped distal portion. In certain embodiments the detachable alignment indicator includes a hollow outer column that connects the cone shaped bottom portion to a first radio-opaque alignment indicator. In other embodiments the detachable alignment indicator includes a hollow outer column that includes a cone shaped distal portion with an opening in the bottommost surface thereof and a proximal portion having a first radio-opaque alignment indicator that includes at least 4 radio-opaque inserts aligned on a top horizontal surface of the detachable alignment indicator in a cross-hair formation. In yet another embodiment the detachable alignment indicator includes a second radio-opaque alignment indicator that is located at distal portion of the detachable alignment indicator. In other embodiments the detachable alignment indicator of the present disclosure includes a proximal radio-opaque alignment indicator connected to a cone shaped distal portion by a radio-opaque inner shaft.

In another aspect of the present disclosure methods for using fluoroscopic needle devices are provided. In one embodiment such a method includes providing a base member and an adhesive layer, whereby the base member has an upper portion including a threaded portion surrounding an opening in the base member, contacting the adhesive layer to a bottom surface of the base member and contacting an opposing surface of the adhesive layer to a subject. Next, a rotatable sphere is seated on the opening in the base member, and a detachable threaded ring that includes a threaded inner surface and a top surface having an opening is attached to the base member. A detachable alignment indicator having a radio-opaque inner shaft and a cone shaped distal portion is then seated on the rotatable sphere. After assembly, a user may rotate the rotatable sphere within the base member using the detachable alignment indicator to align the radio-opaque inner shaft (i.e., needle path) with a pre-identified target in a subject such that the radio-opaque inner shaft is aligned parallel relative to an incident angle of an X-ray beam.

BRIEF DESCRIPTION OF DRAWINGS AND TABLES

FIG. 1 is a side view of an exemplary fluoroscopic needle guide device prior to contacting an adherent layer to a subject, inserting a rotatable sphere into a spherical opening in a base member, affixing a detachable threaded ring to an outer surface of a threaded portion of the base member, and seating a detachable alignment indicator on a tapered recess of the rotatable sphere according to an embodiment of the present disclosure.

Figure 5:
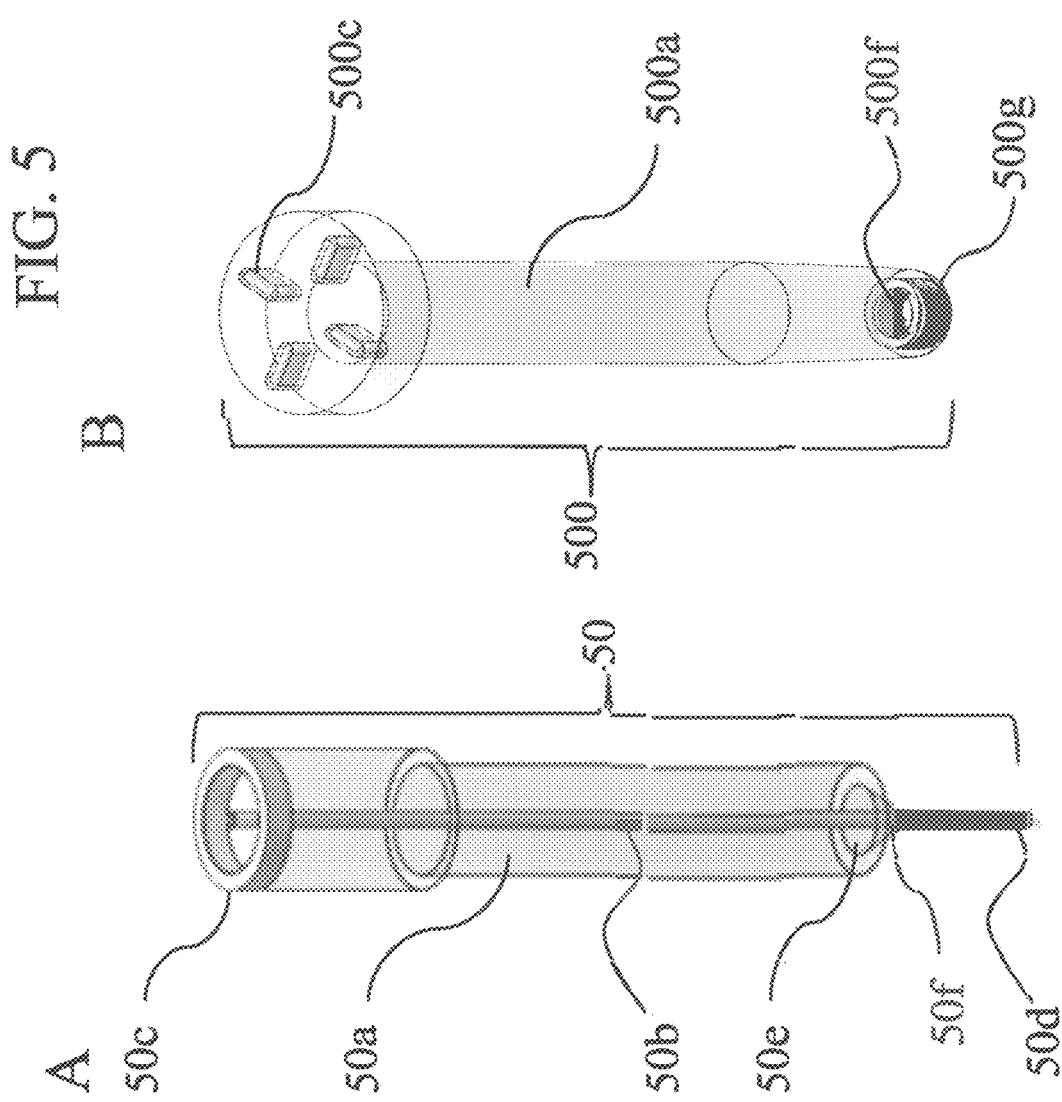

FIG. 5 is a side view of exemplary detachable alignment indicator components of the fluoroscopic needle guide device of the present disclosure. Panel A shows a detachable alignment indicator having a hollow outer column that includes a cone shaped bottom portion with an opening in the bottommost surface thereof. The detachable alignment indicator in Panel A also includes an inner shaft element running through the middle of the hollow outer column and extending through the opening at the bottom of the cone shaped bottom portion thereof. The detachable alignment indicator in Panel A further includes a ring shaped radio-opaque alignment indicator on the topmost surface of the hollow outer column of the detachable alignment indicator. Panel B shows another detachable alignment indicator that includes a hollow outer column that includes a cone shaped bottom portion with an opening in the bottommost surface thereof. The detachable alignment indicator in Panel B also shows an alternative orientation of the radio-opaque alignment indicator, whereby the radio-opaque alignment indicator includes at least 4 radio-opaque inserts aligned on a top horizontal surface of the detachable alignment indicator in a cross-hair formation. The detachable alignment indicator in Panel B further shows an optional second, ring shaped radio-opaque alignment indicator that is located at a bottom portion of the detachable alignment indicator. Panel C shows another exemplary detachable alignment indicator of the present disclosure that includes a proximal ring shaped radio-opaque alignment indicator connected to a circular opening in a cone shaped distal portion by a radio-opaque inner shaft, which passes through the opening in the bottommost surface of the cone shaped distal portion of the detachable alignment indicator.

Figure 6:
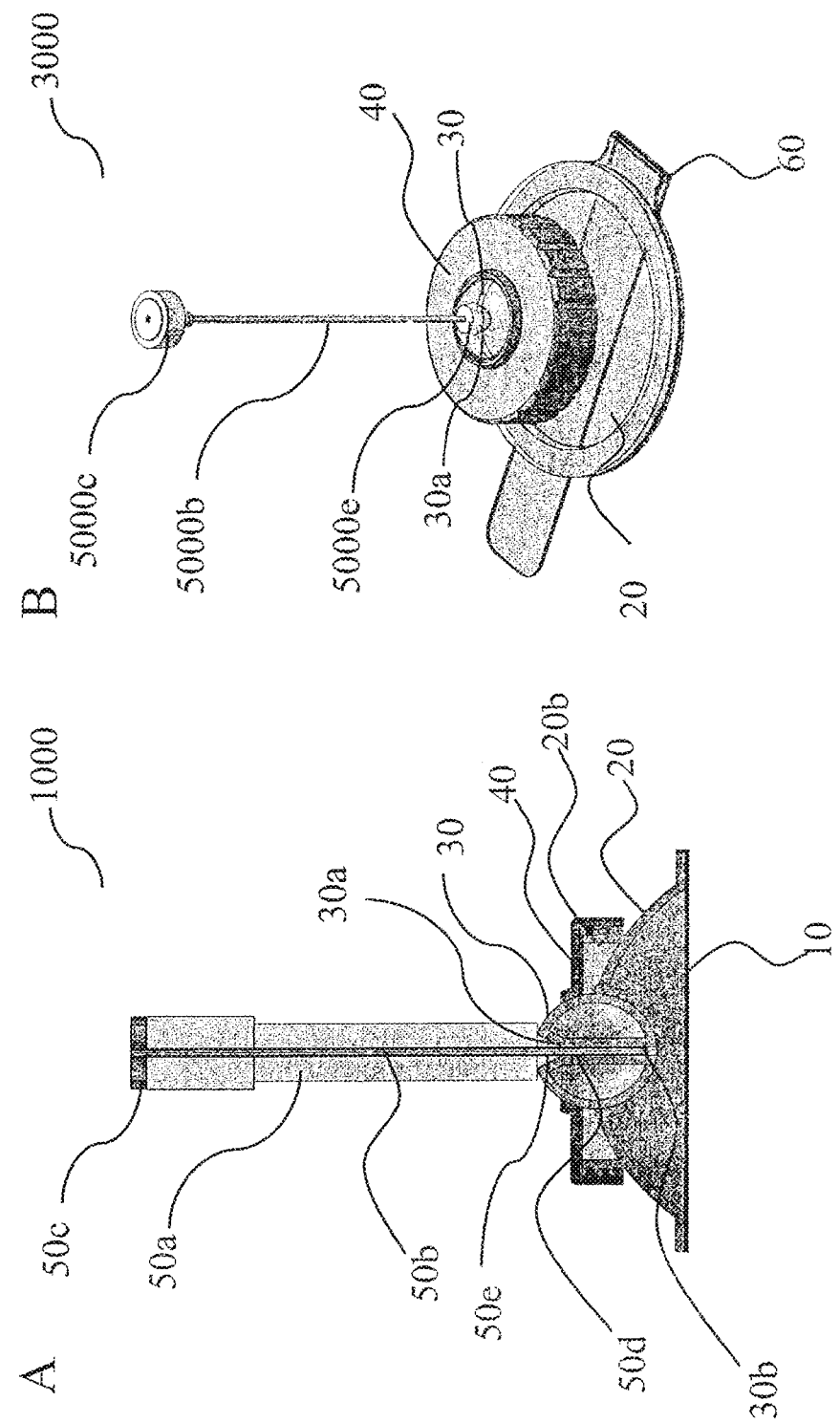

FIG. 6 shows fully assembled exemplary fluoroscopic needle guide devices that include the detachable alignment indicators shown in FIG. 5. Panel A shows a vertical cross-section view of a fully assembled exemplary fluoroscopic needle guide device after a rotatable sphere is inserted into a spherical opening in a base member, a detachable threaded ring is interlocked with an outer surface of a threaded portion of the base member, and a detachable alignment indicator having an outer column portion is seated on a tapered recess of the rotatable sphere, such that a portion of an inner shaft element extends into a channel in the rotatable ball. Panel B shows a side view of a fully assembled exemplary fluoroscopic needle guide device after a rotatable sphere is inserted into a spherical opening in a base member, a detachable threaded ring is interlocked with an outer surface of a threaded portion of the base member, and the cone shaped distal portion of a detachable alignment indicator, which does not include an outer column portion is seated on a tapered recess of the rotatable sphere, such that a portion of an radio opaque inner shaft extends into a guide channel of the rotatable ball.

Figure 7:
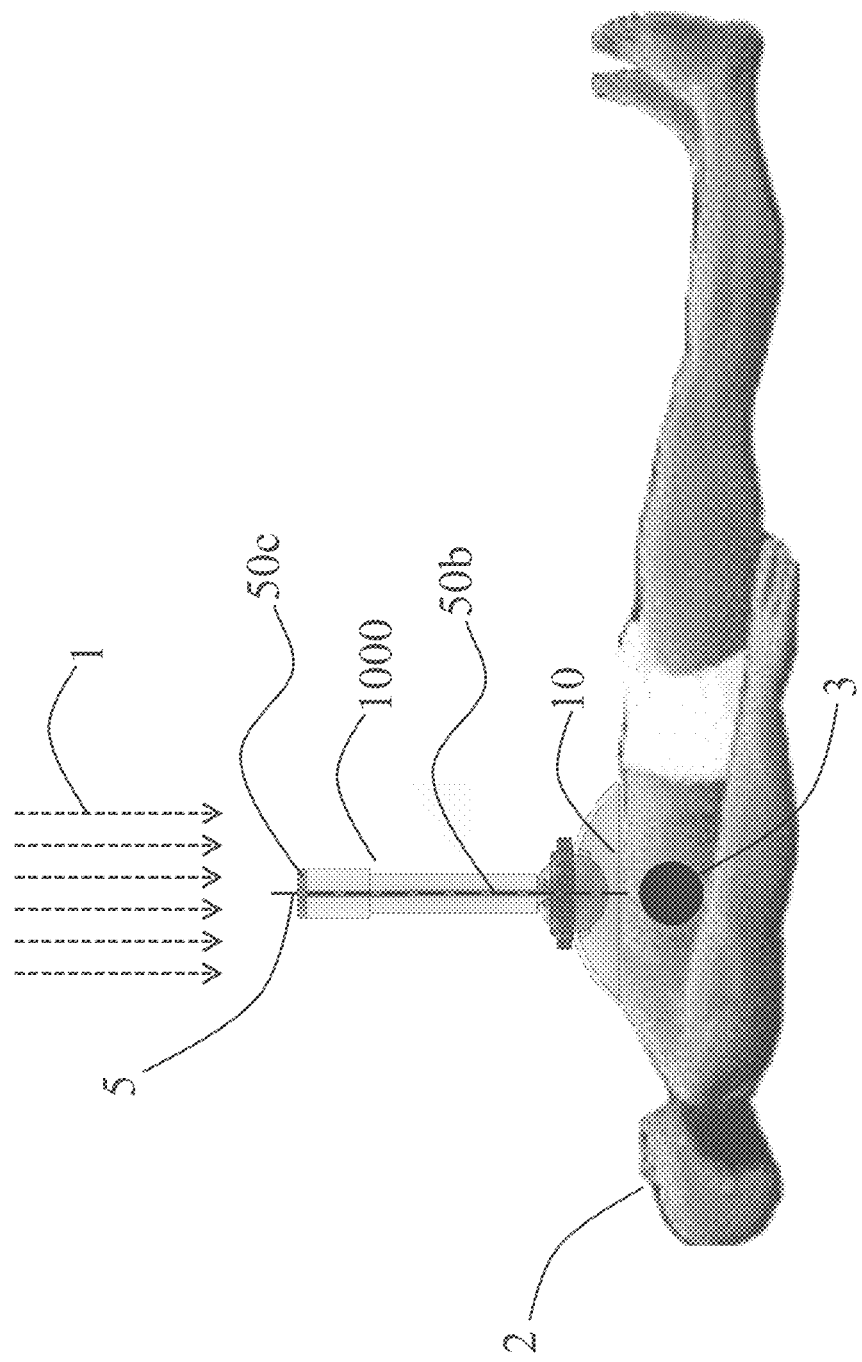

FIG. 7 shows a misaligned fluoroscopic needle guide device, whereby the needle path is properly aligned with the pre-identified target in a subject.

Figure 8:
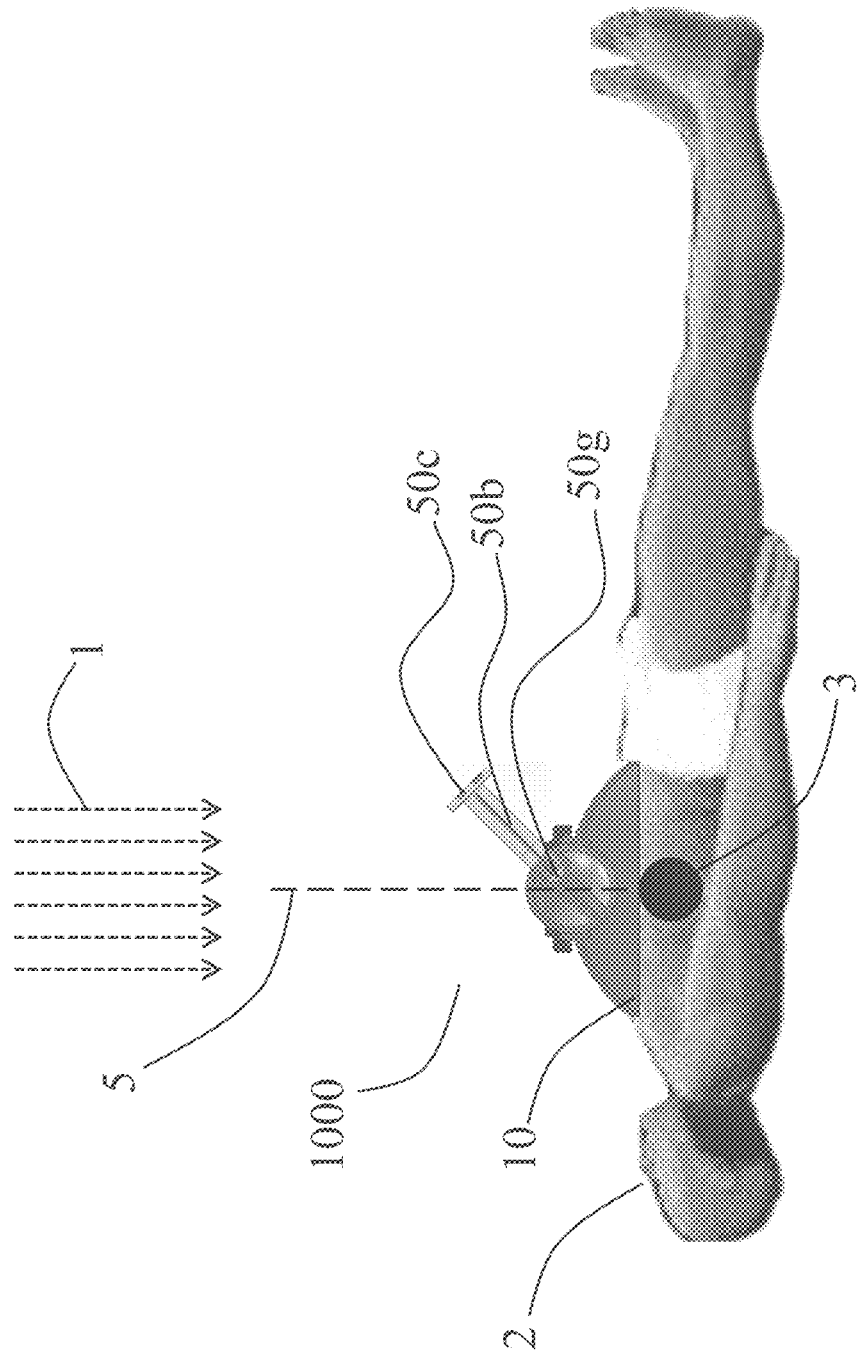

FIG. 8 shows a misaligned fluoroscopic needle guide device, whereby the needle path is not aligned with the pre-identified target in a subject.

FIG. 9 is a top-down view of an exemplary fluoroscopic needle guide device, as seen by a user, after assembly and adhesion to a subject whereby the needle is properly aligned to a pre-identified target (Panel A) and where the needle is misaligned with the target (Panel B).

Figure 10:
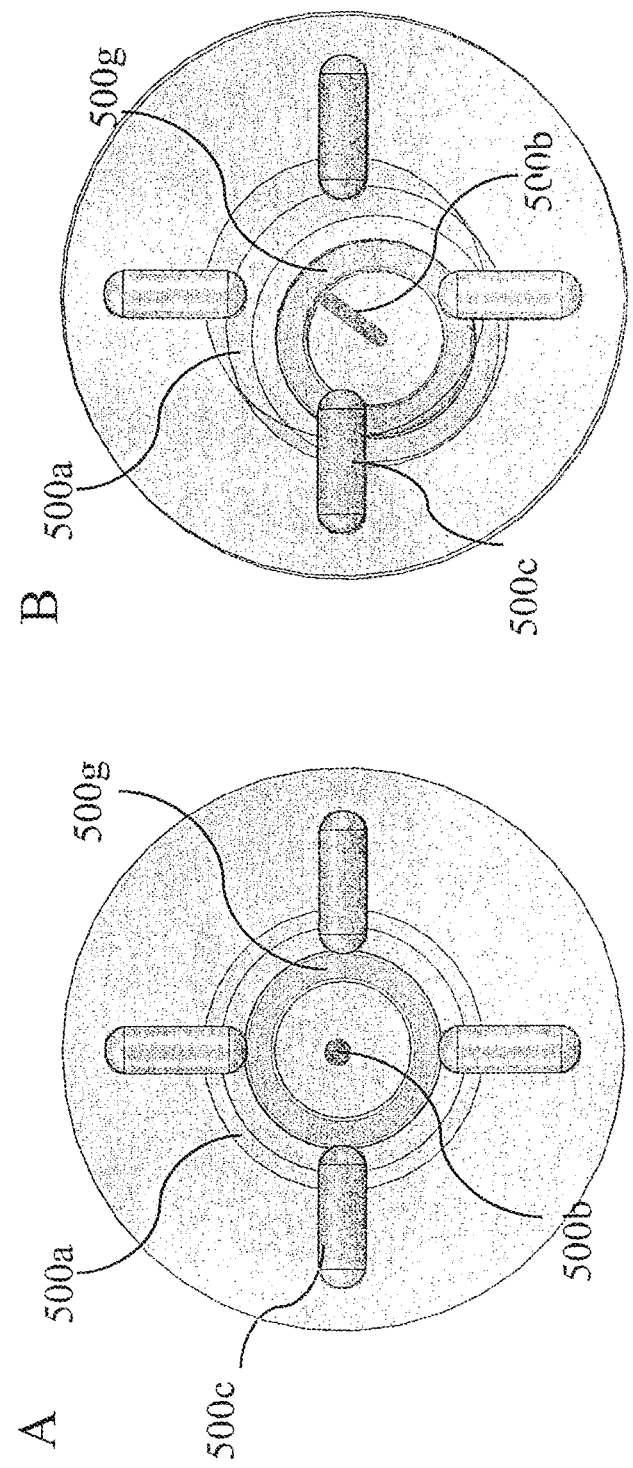

FIG. 10 is a top-down view of an exemplary fluoroscopic needle guide device, as seen by a user that includes a detachable alignment indicator having a first radio-opaque alignment indicator and a second radio-opaque alignment indicator. Panel A depicts the fluoroscopic needle guide device after assembly and adhesion to a subject whereby the needle is properly aligned to a pre-identified target. Panel B shows an example of the fluoroscopic needle guide device where the needle path is misaligned with the pre-identified target according to an embodiment of the present disclosure.

Figure 11:
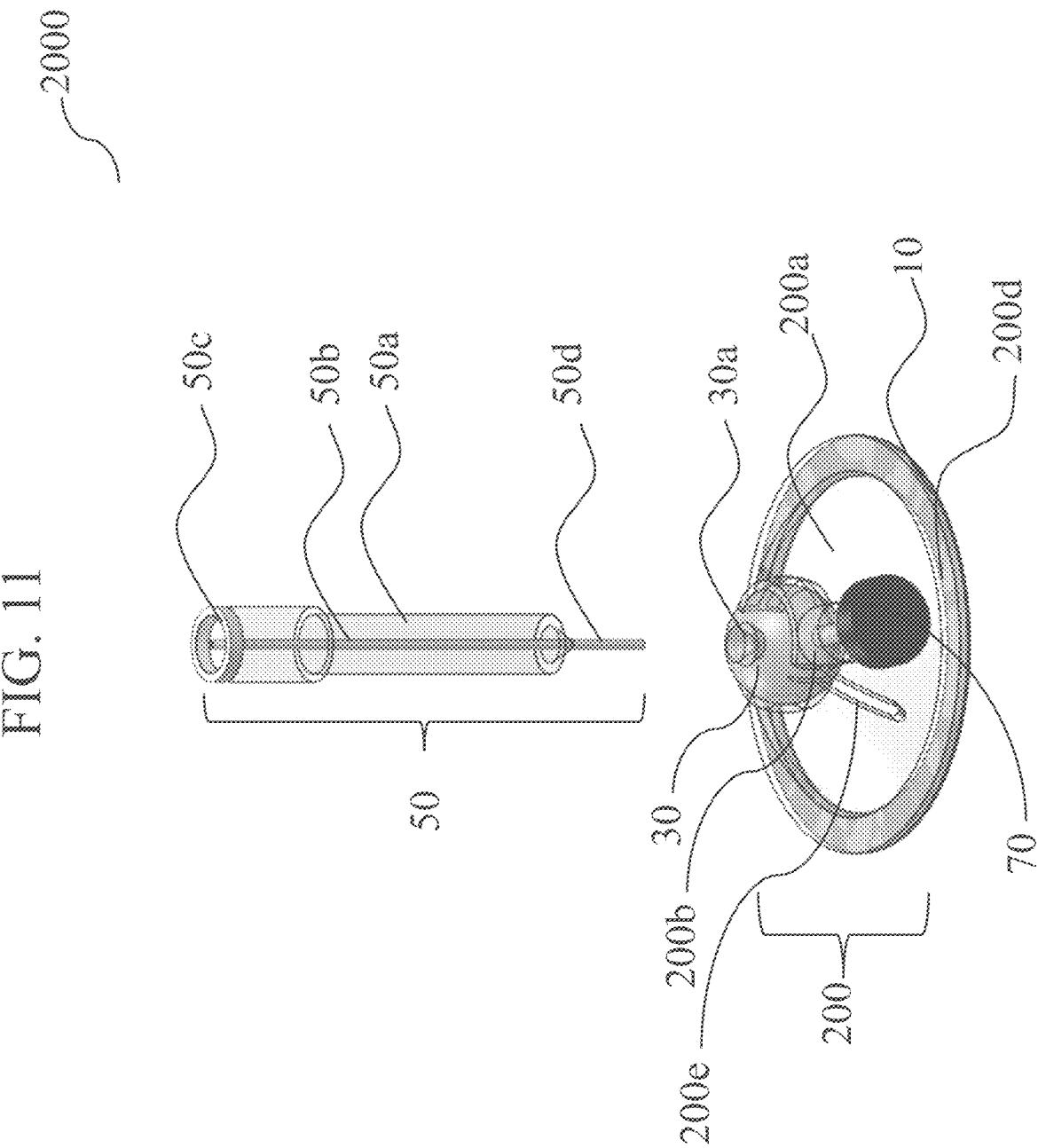

FIG. 11 is a side view of an exemplary fluoroscopic needle guide device according to another embodiment of the present disclosure. The fluoroscopic needle guide device shows a rotatable sphere inserted into a spherical opening in a base member. The base member includes at least one contraction slot in a dome shaped portion of the base member and a cuff that surrounds an opening in the topmost surface of the base member and extends vertically from the topmost surface of the dome portion of the base member. The fluoroscopic needle guide device also includes a screw component that extends through the cuff and contacts an outer surface of the rotatable sphere to prevent further rotation thereof. The fluoroscopic needle guide device also includes a detachable alignment indicator that can be seated on a tapered recess of the rotatable sphere, such that a portion of an inner shaft element extends into a channel in the rotatable ball.

Figure 12:
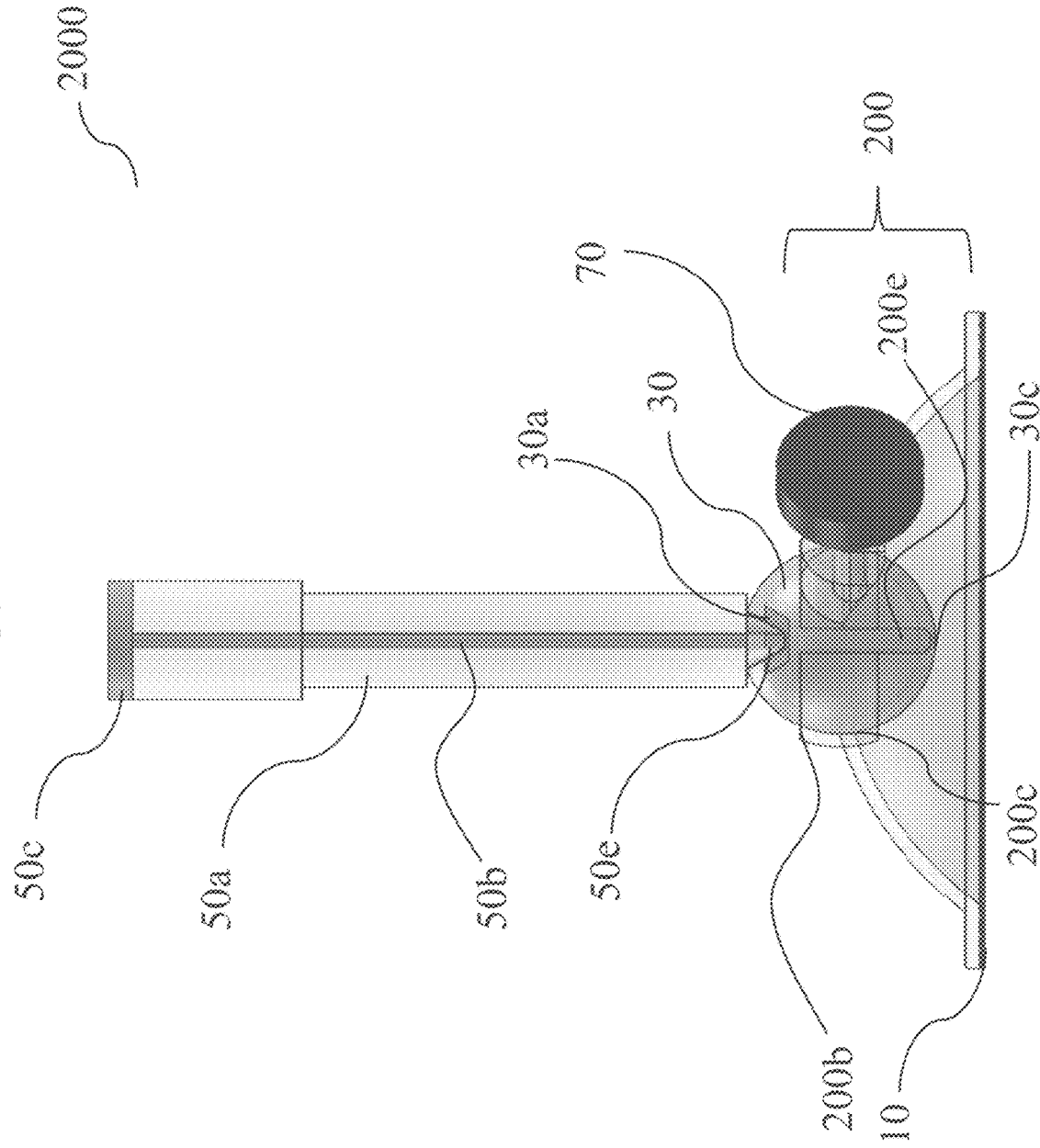

FIG. 12 is a side view of a fully assembled fluoroscopic needle guide device of FIG. 9. The fluoroscopic needle guide device depicts a detachable alignment indicator that is seated on a tapered recess of the rotatable sphere, such that a portion of an inner shaft element extends into a channel in the rotatable ball, and where the rotatable ball is secured by a cuff element and a screw component according to an embodiment of the present disclosure.

Figure 13:
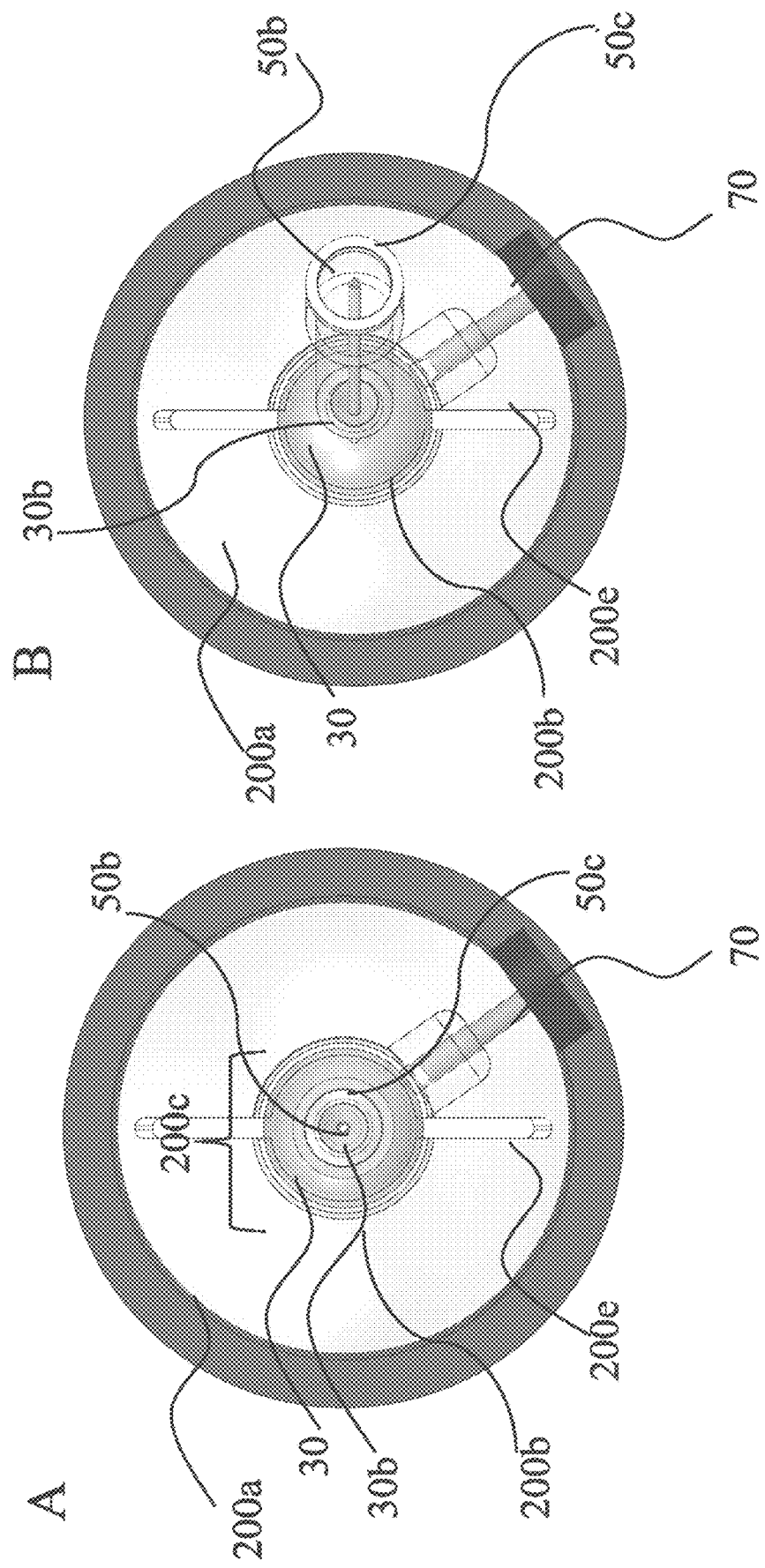

FIG. 13 is a top-down view of the exemplary fluoroscopic needle guide device of FIGS. 9-10 after assembly and adhesion to a subject, as seen by a user, whereby the needle path is properly aligned to a pre-identified target in a subject (Panel A), and where the needle path is misaligned with the target (Panel B).

The drawings are not necessarily drawn to scale. It is noted that like reference numerals refer to like elements across different embodiments.

DETAILED DESCRIPTION OF THE DISCLOSURE

The present disclosure relates to fluoroscopic needle guides for use during a medical procedure, which provides a user with a needle path that maintains a desired needle trajectory throughout the duration of the procedure and methods for using the same. Aspects of the present disclosure are described herein in detail with accompanying figures. As used herein, ordinals such as "first" and "second" are employed merely to distinguish similar elements, and different ordinals may be employed to designate a same element in the specification and/or claims.

It will be understood that when an element is referred to as being "on" or "over" another element of the present disclosure, it can be directly on the other element or intervening elements may also be present. In contrast, when an element is referred to as being "directly on", "directly over" or "in direct physical contact with" another element, there are no intervening elements present. It will also be understood that when an element is referred to as being "connected" or "attached" to another element, it can be directly connected or attached to the other element or intervening elements may be present. In contrast, when an element is referred to as being "directly connected" or "directly attached" to another element, there are no intervening elements present.

One aspect of the present disclosure provides a fluoroscopic needle guide device for use in medical procedures whereby a user, such as a radiologist, clinician or technician, must accurately traverse the tissue of a subject with a medical device, e.g., needle, such that the needle reaches a precise location within the subject.

As used herein, the term "subject" or "patient" refers to any mammal in need of a treatment or medical procedure, such as, for example, fluoroscopy, a needle biopsy or aspiration, injection of an anesthetic. The methods of the current disclosure can be practiced on any mammalian subject in need of a fluoroscopic procedure. Particularly, the devices and methods described herein are most useful when used on humans.

The term "fluoroscopy" or "fluoroscopic procedure", as used herein shall mean a medical procedure that includes a clinician to identify a target site within a subject and position at least one medical device (e.g., needle or catheter) using a fluoroscope such that the at least one medical device will reach the target site located in the patient. A fluoroscope is a device that includes an X-ray emitter coupled to an X-ray detector, whereby the X-ray emitter transmits X-ray beams through a subject. The X-ray emissions are then captured by the X-ray detector and an image is displayed to the clinician, such that the position of any radio-opaque material (e.g., bone, metal, metal containing liquids, medical devices, and needles) are identified, located and defined. Uses of fluoroscopy include, but are not limited to, locating foreign bodies within a subject, needle or aspiration biopsies, and image-guided injections or surgical procedures. More specifically, fluoroscopic applications could include neurosurgical procedures for the placement of intraventricular, subdural or intraparenchymal drains, monitoring or electrical recording devices and electrodes, as well as stimulation electrodes.

In a preferred embodiment of the present disclosure fluoroscopy includes image-guided injections whereby a needle is aligned parallel to the incident angle of an X-ray emitter element of a fluoroscope. The user may then record at least one fluoroscopic image using an X-ray detector to determine the position of the needle relative to a target located within a subject. The user may then adjust the trajectory (i.e., path of the needle) accordingly to ensure that the needle, once inserted into the subject will reach the precise location of the target. Once the user determines that the proper needle path and trajectory are obtained the user will then insert the needle into the subject to a depth sufficient to reach the pre-identified target location.

Figure 1:
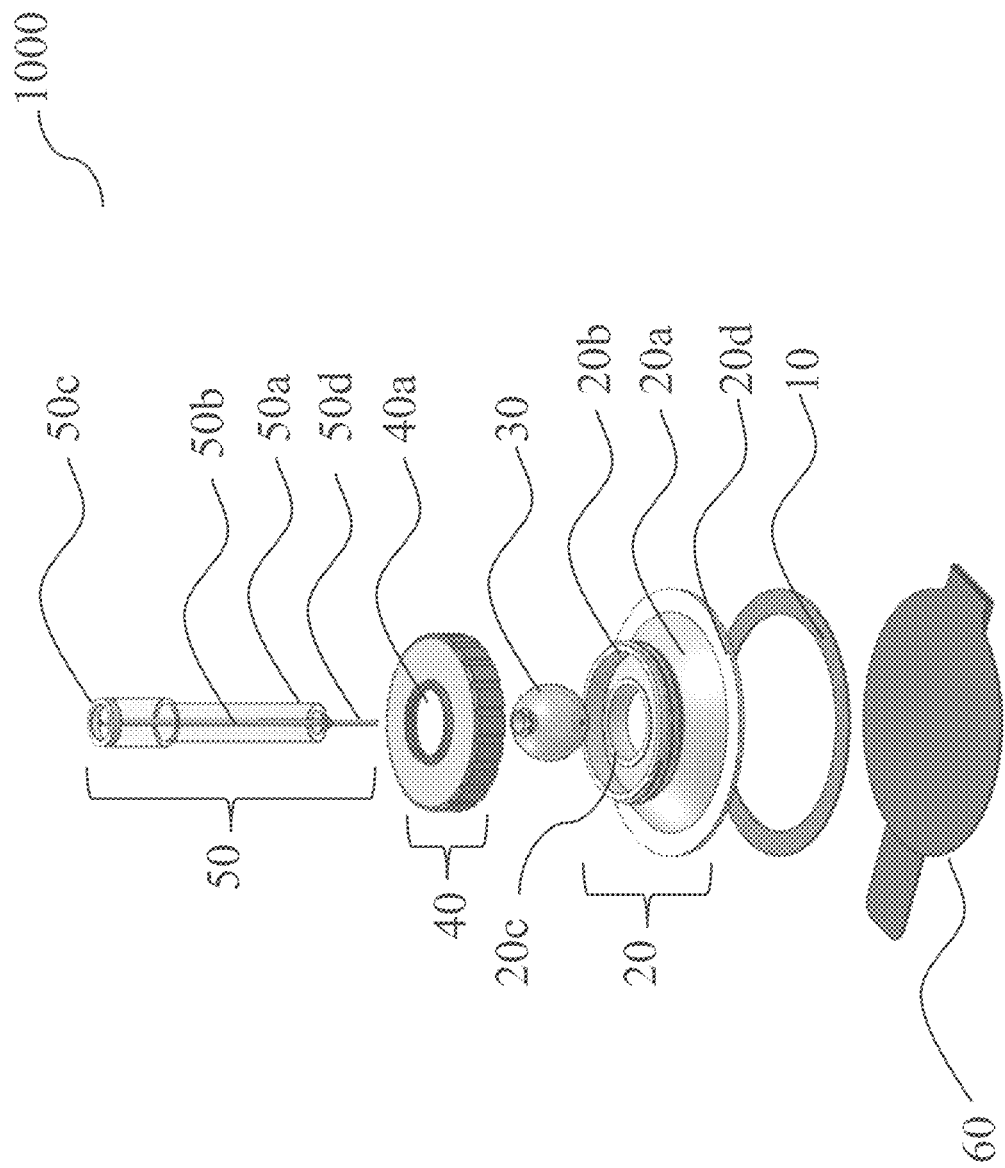
Figure 2:
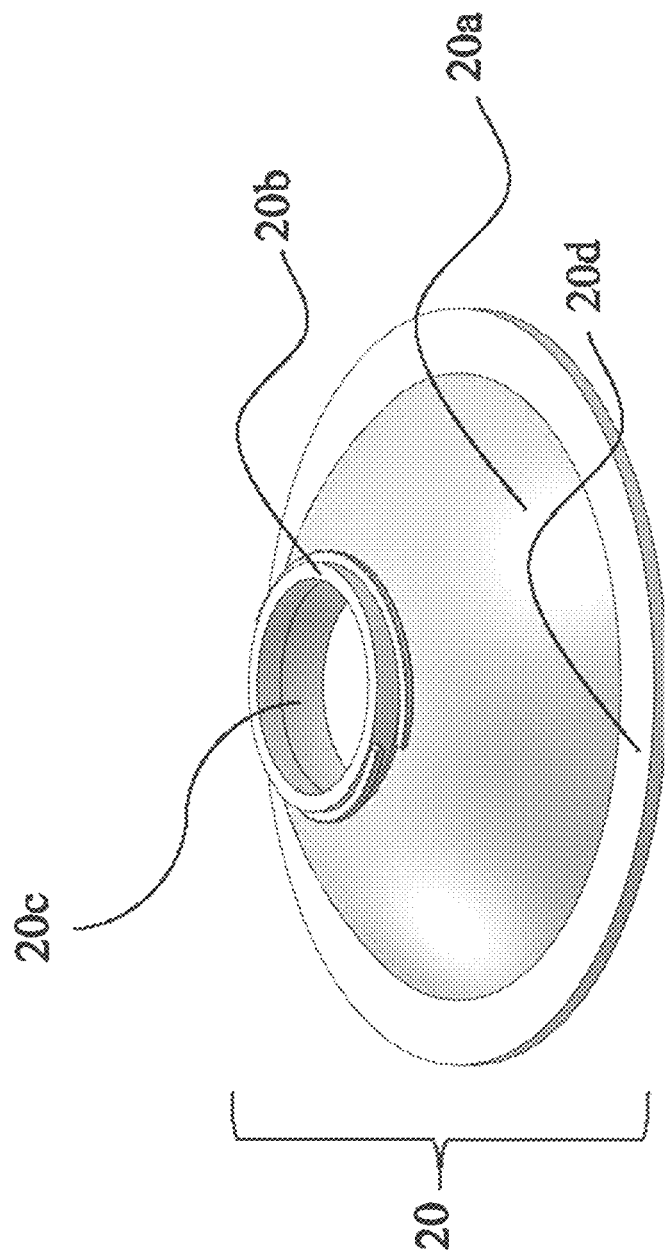
FIG. 2 is a side view of an exemplary base member element of the fluoroscopic needle guide device, which includes a dome shaped upper portion having a threaded portion that surrounds a spherical opening in a top portion of the base member.

FIGS. 1-6 show a fluoroscopic needle guide device (1000, 3000) according to one embodiment of the present disclosure. Referring to FIG. 1, an exemplary fluoroscopic needle guide device includes an adhesive layer (10) interspersed between a top surface of a release liner (60) and a bottom surface of a base member (20). The release liner (60) can include any material having at least one wax or silicon coated surface, such that the release liner can contact an entire lateral surface of the adhesive layer and be subsequently released by a user without altering the ability of the adhesive layer to adhere to a substrate. For example, the release liner (60) can include a polyethylene, such as low density polyethylene (LPDE) film, high density polyethylene material (HPDE), or paper, poly-coated paper, polyester film or silicon coated or fluoropolymer coated layers thereof. The adhesive layer (10) can include any material capable of holding two or more objects together by direct surface contact. For example, adhesive layer (10) can include any acrylic, acrylate or silicon adhesive capable of adhering to skin or other mammalian tissue, such as a polyethylene film that is coated on both sides with an acrylic adhesive that is EtO and Gamma stable.

In certain embodiments, the base member (20) includes a bottom portion (20*d*) in direct contact with an upper portion (20*a*) of the base member. The bottom portion of the base member (20*d*) can include a horizontal surface to which an adhesive layer (10) can be connected. The upper portion of the base member (20*a*) extends vertically above a topmost plane of the bottom portion of base member (20*d*) and includes a hole or opening (20*c*) in a top surface of the base member.

In a specific embodiment of the present disclosure, the upper portion of the base member (20*a*) includes a threaded portion (20*b*) that extends upward from an outer surface of the base member surrounding the opening. For example, as shown in FIG. 1, the topmost surface of the threaded portion (20*b*) of the base member extends above a topmost plane of the opening (20*c*) of the upper portion of the base member (20*a*). As exemplified in FIG. 2, in some embodiments the topmost surface of the opening in said base member (20*c*) is coplanar with the topmost surface of the threaded portion of the base member (20*b*).

Referring to FIGS. 11-13, a fluoroscopic needle guide device (2000) according to another embodiment of the present disclosure includes a base member (200) including a bottom portion (200*d*) attached to an upper portion (200*a*) of the base member. As shown, in FIG. 11 the bottom portion of the base member (200*d*) includes a horizontal surface to which an adhesive layer (10) can be affixed. The upper portion of the base member (200*a*) extends vertically above a topmost plane of the bottom portion of base member (200*d*) and includes at least one elongated opening (200*e*) that enables compression or expansion of the upper portion of the base member. The upper portion of the base member (200a) can also include a circular or spherical opening (200c) in a top surface of the base member (200). The upper portion of the base member (200a) further includes a contact ring (200b) that extends upward from an outer surface of the base member surrounding the circular opening or spherical opening (200c). The contact ring (200b) includes a bottom surface that is affixed to the upper portion of the base member (200a), and raised sidewalls that surround the circular or spherical opening (200c) of the upper portion of the base member (200a), which has at least one threaded opening (e.g. nut) for which a screw element (70) can be affixed. In another embodiment the contact ring (200b) includes two raised portions affixed to the upper portion of the base member (200a), whereby each raised portion is located on opposing sides of an elongated opening (200e) such that the raised sidewalls of each raised portion surround the circular or spherical opening (200c) in the upper portion of the base member (200a), as shown in FIGS. 11-13. In certain embodiments at least one of the raised sidewalls surrounding the circular or spherical opening of the upper portion of the base member (200a) includes a threaded opening (e.g. a nut) for which a screw element (70) can be affixed.

Generally, the base member may include any radio-lucent material. As used herein, the term "radio-lucent" means any material or combination of materials that are transparent or transradiant to electromagnetic radiation, i.e., permit the passage of X-rays. Specifically, exemplary radio-lucent materials for use in the present disclosure including but are not limited to, polymers such as plastics and thermoplastic resins, or carbon and carbon-fiber composites.

The term "radio-opaque" as used in the present disclosure shall mean any material or combination of materials capable of obstructing X-rays. More specifically, exemplary radio-opaque materials include, but are not limited to, metals such as aluminum, stainless steel, or titanium.

The base member is composed of a radio-lucent material. In certain embodiments the radio-lucent material includes a thermoplastic polymer such as, for example, polycarbonate, polypropylene, polystyrene, polyethylene, neoprene, silicon and polyvinyl chloride (PVC). In a preferred embodiment the base member includes acrylonitrile butadiene styrene (ABS) or polylactic acid (PLA) that is EtO and Gamma stable.

Figure 3:
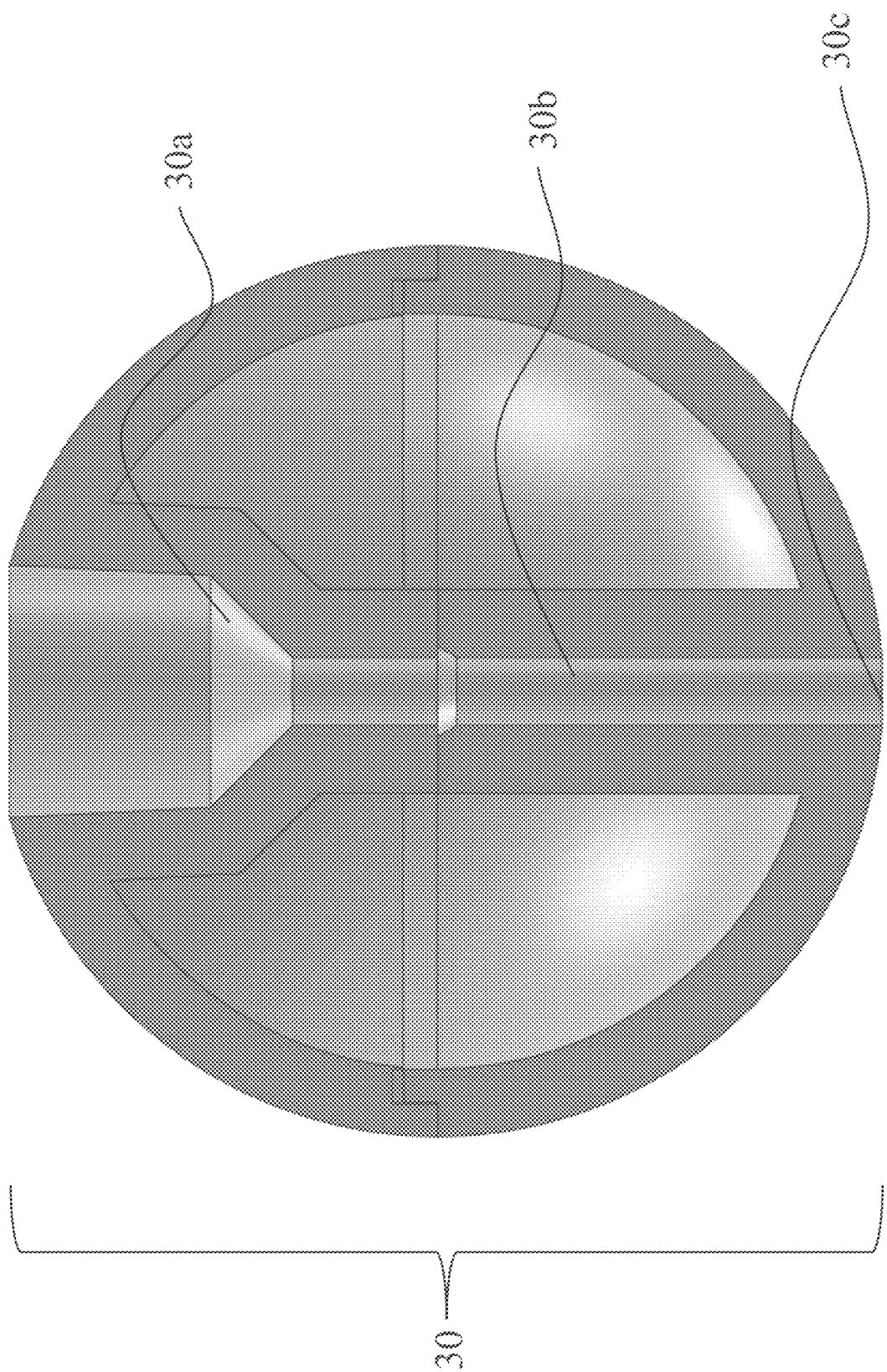
FIG. 3 is a vertical cross-sectional view of a rotatable sphere element of the exemplary fluoroscopic needle guide device that includes a top portion having a tapered recess and a guide channel that traverses the diameter of the rotatable sphere and connects the bottommost portion of the tapered recess to an opening in the bottommost surface of the rotatable sphere.

Referring to FIG. 3 an exemplary rotatable sphere (30) for use in a fluoroscopic needle guide device of the present disclosure is shown. In certain embodiments of the present disclosure, the rotatable sphere element (30) includes an upper portion located above the horizontal equator of the rotatable sphere (30) and lower portion that is located below the horizontal equator of the rotatable sphere (30) that are interlocking. In another embodiment, the rotatable sphere element (30) of the present disclosure is of solid construction, i.e., a single piece of material. In yet another embodiment the rotatable sphere (30) has an outer wall and an inner wall that encapsulate (e.g., completely surround) at least one open space, e.g., air pocket. In some embodiments the diameter of rotatable sphere (30) is between 5 mm and 25 mm. In a preferred embodiment the diameter of the rotatable sphere (30) is 10 mm in diameter. In another preferred embodiment, the diameter of the rotatable sphere (30) is 7 mm, 8 mm, 9 mm, 11 mm, 12 mm, 13 mm, 14 mm, 15 mm in diameter.

In a preferred embodiment, both the upper portion and lower portion of the rotatable sphere (30) are traversed by a hollow guide channel (30c) through which a medical device, such as a needle, can pass. In specific embodiments the hollow guide channel (30c) has a diameter that is equal to or greater than that of a medical device, such as a catheter, drain or electrode. In certain embodiments, the guide channel has a diameter that is equal to that of a needle. In specific embodiments, the diameter of the hollow guide channel (30c) corresponds to the diameter of a 14, 15, 16, 17, 18, 19, 20, 21, 22, 23, 24 or 25 gauge needle. In other embodiments the diameter of the guide channel (30c) is between 0.5 mm and 2.5 mm, inclusive. In yet another embodiment, the diameter of the guide channel is 2.2 mm, 1.9 mm, 1.7 mm, 1.5 mm, 1.3 mm, 1.1 mm, 1 mm, 0.9 mm 0.85 mm, 0.75 mm, 0.65 mm, 0.7 mm, 0.6 mm, or 0.55 mm.

In certain embodiments, the rotatable sphere (30) includes a tapered recess (30a) located at a top surface of the upper portion of the rotatable sphere. The tapered recess (30a) includes vertical outer sidewalls surrounding a recessed circular upper portion of the tapered recess (30a). In certain embodiments, the tapered recess (30a) also includes a lower portion that is cone shaped, which has an upper width that is greater than lower the width of a bottom portion of the cone shaped lower portion of the tapered recess (30a). In a preferred embodiment, the tapered recess coincides with the cone shaped distal portion (50e) of a detachable alignment indicator (50, 500, 5000), which is described below.

In one embodiment, the rotatable sphere (30) includes an opening in the bottommost surface of the rotatable sphere (30c) that permits a medical device (e.g., needle) to pass through the channel and pass through the bottom most surface of the rotatable sphere (30). The opening (30c) is defined such that the opening (30c) allows a needle or radio-opaque inner stem (50, 500, 5000) to exit the rotatable sphere (30) and pass through a bottommost surface of the fluoroscopic needle guide device into a subject. As shown in FIG. 3, a rotatable sphere of the present disclosure includes a top portion consisting of a tapered recess (30a) that is connected to an opening in the bottommost surface of the rotatable sphere (30c) opposite the tapered recess (30a) by a guide channel (30b) through which material or a medical device, such as a needle may pass (i.e., needle path).

The rotatable sphere (30) can be composed of a radio-lucent material that is EtO and Gamma radiation stable. In certain embodiments, the radio-lucent material includes a thermoplastic polymer that has high stiffness, stability and strength with low friction. Non-limiting examples of materials that can be used in a rotatable sphere (30) of the present disclosure are polycarbonate, polypropylene, polystyrene, polyethylene, polyoxymethylene (e.g., acetal resin or Delrin®, neoprene, silicon and polyvinyl chloride (PVC). In a preferred embodiment the rotatable sphere (30) includes acrylonitrile butadiene styrene (ABS), polylactic acid (PLA) or polyoxymethylene. In a specific embodiment, the rotatable sphere includes a radio-lucent material that is EtO and Gamma stable. In certain embodiments, the outermost surface of the rotatable sphere (30) is lubricated with an lubricant oil or the like to reduce friction between the outermost surface of the rotatable sphere (30), the base member (20) and a detachable threaded ring (40). Lubricants for use in the present disclosure will be commonly known by one of ordinary skill in the art.

Figure 4:
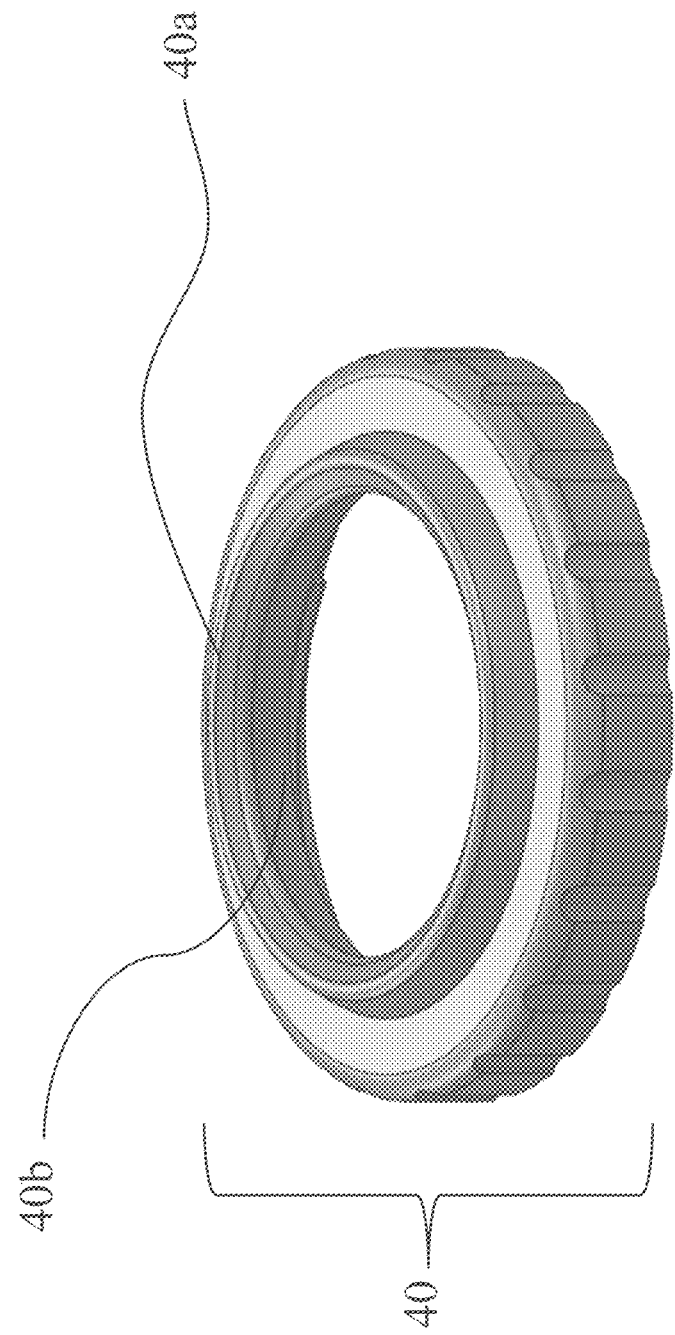
FIG. 4 is a side view of a detachable threaded ring component of the exemplary fluoroscopic needle guide device that includes threaded innermost vertical sidewalls and a horizontal top surface having a spherical opening for securing a rotatable sphere.

FIG. 4 of the present disclosure shows an exemplary detachable threaded ring (40) for use in a fluoroscopic needle guide device of the present disclosure. In one embodiment, of the present disclosure the detachable threaded ring element (40) includes an inner sidewall having a threaded outer surface (40b), which corresponds to the threading on the threaded portion of the base member (20b), such that when contacted the user may interlock the base member (20) and the detachable threaded ring (40) by manually turning the detachable threaded ring (40) in a clockwise manner.

In certain embodiments, the detachable threaded ring (40) also includes a textured outermost vertical sidewall (40c) that can be gripped by an end user in order to align and interlock the threaded innermost sidewall surface (40b) of the detachable threaded ring with the threaded portion (20b) of the base structure (20). In other embodiments, the outermost vertical sidewall surface (40b) of the detachable threaded ring (40) is smooth [not shown]. The detachable threaded ring also includes an opening (40a) in a topmost horizontal surface of the detachable threaded ring, in which the rotatable sphere (30) can be seated. In some embodiments, the diameter of opening (40a) is between about 0.5 mm and 2.5 mm, inclusive. In yet another embodiment, the diameter of the opening (40a) is about 2.2 mm, 1.9 mm, 1.7 mm, 1.5 mm, 1.3 mm, 1.1 mm, 1 mm, 0.9 mm. 0.85 mm, 0.75 mm, 0.65 mm, 0.7 mm, 0.6 mm, or 0.55 mm.

The detachable threaded ring (40) can be composed of a radio-lucent material. In certain embodiments, the radio-lucent material includes a thermoplastic polymer such as, for example, polycarbonate, polypropylene, polystyrene, polyethylene, neoprene, silicon and polyvinyl chloride (PVC). In a preferred embodiment, the base member includes acrylonitrile butadiene styrene (ABS) or polylactic acid (PLA). In a specific embodiment the detachable threaded ring (40) includes a radio-lucent material that is EtO and Gamma stable.

FIG. 5, panels A-C show exemplary alignment indicators (50, 500, 5000) for use in the fluoroscopic needle guide device of the present disclosure. As shown in FIG. 5, panel A, in one embodiment of the present disclosure the detachable alignment indicator (50) includes an outer column portion (50a) that connects a proximal end including a circular opening to a cone shaped distal portion (50e) that can be seated in the tapered recess of the rotatable sphere (30a). The bottommost surface of the cone shaped distal portion includes a circular opening (50f) that can permit a radio-opaque inner shaft (50b) to exit through the opening in the distal portion of the detachable alignment indicator (50) and enter into the hollow guide channel (30c) within the rotatable sphere. The opening in the bottommost surface of the cone shaped distal portion (50f) of the detachable alignment indicator (50) is defined such that the opening allows a needle or a portion of the radio-opaque inner shaft (50d) to exit the detachable alignment indicator (50) and pass into the hollow guide channel (30c) of the rotatable sphere. In a preferred embodiment, the outer column portion of the detachable alignment indicator (50a) includes a proximal portion having an upper width that is greater than the width of the distal portion of the lower the width of a bottom portion of the detachable alignment indicator (50). As shown in FIG. 5, panel B in certain embodiments the width of the outer column portion (500a) of the detachable alignment indicator is uniform in diameter.

The outer column portion (50a, 500a) and cone shaped distal end (50e, 500e, 5000e) of the detachable alignment indicator can be composed of a radio-lucent material that is EtO and Gamma stable. In certain embodiments, the radio-lucent material includes a thermoplastic polymer such as, for example, polycarbonate, polypropylene, polystyrene, polyethylene, neoprene, silicon and polyvinyl chloride (PVC). In a preferred embodiment, the outer column portion (50a, 500a) and cone shaped distal end (50e, 500e, 5000e) of the detachable alignment indicator includes acrylonitrile butadiene styrene (ABS) or polylactic acid (PLA). In a specific embodiment the outer column portion (50a, 500a) and cone shaped distal end (50e, 500e, 5000e) of the detachable alignment indicator includes EtO and Gamma stable acrylonitrile butadiene styrene (ABS) or polylactic acid (PLA).

In certain embodiments, a portion of the radio-opaque inner shaft may extend into a portion (50d, 5000d) of the hollow guide channel (30c) of the rotatable sphere. In other embodiments the radio-opaque inner shaft (50b, 5000b) passes through the opening in the bottommost surface of the cone shaped distal portion (50f, 50000f) of the detachable alignment indicator (50, 5000) and traverses the entire hollow guide channel (30c) of the rotatable sphere (30). The radio-opaque inner shaft (50b, 500b, 5000b) may be connected to or directly attached to the detachable alignment indicator (50, 5000) or can be removable. In some embodiments the radio-opaque inner shaft (50b, 500b, 5000b) can be hollow tube. In other embodiments the radio-opaque inner shaft (50b, 500b, 5000b) is a solid cylinder.

The radio-opaque inner shaft (50b, 500b, 5000b) is composed of any radio-opaque material known by one of ordinary skill in the art. Non-limiting examples of radio-opaque materials for use in the radio-opaque inner shaft (50b, 500b, 5000b) include metals. In a specific embodiment of the present disclosure, the radio-opaque inner shaft includes Gamma stable stainless steel. However, radio-opaque materials cannot include inks or pigments due to their instability during the sterilization process and exposure to Gamma or X-rays.

In a preferred embodiment, the proximal end of the detachable alignment indicator (50, 500) includes at least one radio-opaque alignment indicator (50c, 500c, 5000c). As shown in FIG. 5, panel A, the proximal end of the detachable alignment indicator includes only one radio-opaque alignment indicator, i.e., first radio-opaque alignment indicator (50c). In certain embodiments, the first radio-opaque alignment indicator (50c) overlays the entire upper most surface of the proximal end of outer column portion (50a) of the detachable alignment indicator. In a specific embodiment, the first radio-opaque alignment indicator (50c) is ring shaped.

In another embodiment, the radio-opaque alignment indicator (500c) includes radio-opaque inserts (500c) that are aligned on opposing sides of the outer column of the detachable alignment indicator (500a). In certain embodiments, the radio-opaque alignment indicator includes at least 2, at least 3, at least 4, at least 5, or at least 6 radio-opaque inserts that are aligned perpendicular to the outermost surface of the proximal end outer column of the detachable alignment indicator (500a). In a specific embodiment, the radio-opaque alignment indicator includes at least 4 radio-opaque inserts that are embedded within an upper horizontal surface of the detachable alignment indicator (500a), and are aligned perpendicular to the outermost surface of the outer column of the detachable alignment indicator (500a) in a cross-hair formation, as shown in FIG. 5B.

Referring to FIG. 5, panel B, in certain embodiments of the present disclosure the detachable alignment indicator (500a) can include another radio-opaque alignment indicator (500g), i.e., second radio-opaque alignment indicator. The first radio-opaque alignment indicator (500c) and second radio-opaque alignment indicator (500g) are configured such that the center portion of each radio-opaque alignment indicators are aligned (i.e., vertically coincident). Specifically, the first radio-opaque alignment indicator (500c) and second radio-opaque alignment indicator (500g) are configured such that a radio-opaque inner shaft (500b) [not shown] traverses the center of each of the first radio-opaque alignment indicator and second radio-opaque alignment indicator and passes through the opening in the cone shaped distal end (500e) of the detachable alignment indicator. In certain embodiments, the second radio-opaque alignment indicator includes a ring shaped radio-opaque material that lines the topmost surface of the cone shaped distal portion (5000 of the detachable alignment indicator (500). In a specific embodiment, the second radio-opaque alignment indicator (500g) includes a ring shaped radio-opaque material that is in direct contact with an entire inner sidewall of the outer column of the detachable alignment indicator (500a). In a specific embodiment, the first radio-opaque alignment indicator (500c) is ring shaped.

The radio-opaque alignment indicator(s) (50c, 500c, 500g, 5000c) of the present disclosure can be composed of any radio-opaque material known by one of ordinary skill in the art. Non-limiting examples of radio-opaque materials for use in the radio-opaque alignment indicator(s) include metals. In a specific embodiment of the present disclosure, the radio-opaque alignment indicator(s) consists of Gamma stable stainless steel. However, the radio-opaque materials of the alignment indicator(s) cannot include inks or pigments due to their instability during the sterilization process and exposure to Gamma or X-rays.

As shown in FIG. 5, panel C, in one embodiment of the present disclosure the detachable alignment indicator (5000) does not include an outer column portion (50a, 500a). The detachable alignment indicator (5000) includes a proximal ring shaped radio-opaque alignment indicator (5000c) connected to a circular opening (5000f) in a cone shaped distal portion (5000e) by a radio-opaque inner shaft (5000b), which passes through the opening in the bottommost surface of the cone shaped distal portion (5000f) of the detachable alignment indicator (5000) and traverses the entire hollow guide channel (30c) of the rotatable sphere (30) when the cone shaped distal portion (5000e) is seated in the tapered recess of a rotatable sphere (30a). The opening in the bottommost surface of the cone shaped distal portion (50000 of the detachable alignment indicator (5000) is defined such that the opening allows a needle or a portion of the radio-opaque inner shaft (5000d) to exit the bottommost surface of the cone shaped distal portion (50000 and pass into the hollow guide channel (30c) of the rotatable sphere. In one embodiment the proximal ring shaped radio-opaque alignment indicator (5000c) surrounds an entire outermost surface of a radio-lucent portion of the proximal portion of the detachable alignment indicator, which includes a circular opening that is connected to the radio-opaque inner shaft (5000b) of the detachable alignment indicator (5000).

Referring to FIG. 6, which shows two fully assembled fluoroscopic needle guide devices of the present disclosure that can include any of the exemplary detachable alignment indicators shown in FIG. 5. The fluoroscopic needle guide device shown in panel A includes a base member (20) having a circular opening in an upper surface thereof and a threaded portion (20b) that interlocks with the threaded inner surface (40b) of the detachable threaded ring (40). Seated in the circular opening of the base member (20) is a rotatable sphere (30), which includes an upper portion having a tapered recess (30a) and an opening (30b) that are connected by a guide channel (30c) through which a needle or the radio-opaque inner shaft of the detachable alignment indicator (50b) can traverse. The rotatable sphere (30) is secured by placing the detachable threaded ring (40) over the upper portion of the rotatable sphere (30) such that a circular opening in the topmost surface of the detachable threaded ring (40a) is vertically aligned with the circular opening in the base member (20b). The threaded inner surface (40b) of the detachable threaded ring (40) is interlocked (e.g., a clockwise rotation of the detachable threaded ring) with an outer surface of a threaded portion of the base member (20b). Continued tightening of the detachable threaded ring enables the user to adjust the friction between the rotatable ball (30) and the innermost surface of the opening of the detachable threaded ring (40a), whereby more friction between the detachable threaded ring (40) and the outermost surface of the rotatable ball (30) limits movement of the rotatable sphere (30) when a needle or a detachable alignment indicator (50, 500, 5000) is attached. In other embodiments, the detachable threaded ring (40a) can be loosened (i.e., rotated counter clockwise) by a user in order to reduce the friction between the detachable threaded ring (40) and the outermost surface of the rotatable sphere (30), which enables more fluid rotation of the rotatable sphere (30).

After assembly of the base member (20), the rotatable sphere (30) and the detachable threaded ring (40), a user may seat a detachable alignment indicator (50, 500, 5000) as shown in FIG. 6 within the tapered recess of the rotatable sphere (30a). More specifically, the detachable alignment indicator (50, 500, 5000) is seated such that the cone shaped distal portion of the detachable alignment indicator (50e, 500e, 5000e) is seated on the tapered recess of the rotatable sphere (30a), whereby the portion of an radio-opaque inner shaft (50b, 500b, 5000b) that extends through an opening in the cone shaped distal portion of the detachable alignment indicator (50d, 500d, 5000d) is positioned within the guide channel of the rotatable sphere (30c). As shown in FIG. 6, panel A, in certain embodiments the detachable alignment indicator (50, 500, 5000) can have an outer column portion. In other embodiments, as shown in FIG. 6, panel B the detachable alignment indicator (50, 500, 5000) includes a proximal ring shaped radio-opaque alignment indicator (5000c) connected to a circular opening (50000 in a cone shaped distal portion (5000e) by a radio-opaque inner shaft (5000b).

In one aspect of the present disclosure, a user, such as a physician, veterinarian, scientist or clinician contact the adhesive layer (10) of the base member to a subject and use the fluoroscopic needle guide devices of the present disclosure in a medical procedure, veterinary procedure, or research protocol. More specifically, a clinician may use the fluoroscopic needle guide devices of the present disclosure to determine: needle placement for tissue biopsy, needle placement of an injection (e.g., therapeutic, diagnostic or anesthetic agent), needle placement for ablative therapy, percutaneous device implantation, or orthopedic hardware insertion.

FIG. 7 shows one embodiment of the present disclosure, whereby a user attaches an adhesive layer (10) located on the bottommost surface of the base member (20) to an outer surface of a subject (2) (e.g., skin). In certain embodiments the user may pre-assemble the base member (20), the rotatable sphere (30) and detachable threaded ring (40) prior to affixing the base member to the subject. In yet another embodiment, the user may affix the base member to an outer surface of the subject and then assemble the base member (20), the rotatable sphere (30) and the detachable threaded ring (40). Once the base member (20) is adhered to the subject (2) and assembled, a detachable alignment indicator (50, 500, 5000) is securely seated within the tapered recess of the rotatable sphere (30a) allowing the user to rotate the rotatable sphere (30) such that the radio-opaque inner shaft (50b, 500b, 5000b), which provides the needle or device path (i.e., trajectory) is aligned with a pre-identified target in a subject (3).

As shown in FIG. 7, once the fluoroscopic needle guide (1000) is positioned on the surface of a subject (3) X-rays (1) are projected onto the fluoroscopic needle guide (1000) from an X-ray emitter device. The user then rotates the rotatable ball (30) using the detachable alignment indicator (50) such that the radio-opaque inner shaft (50b) is aligned with the pre-identified target site (3) within the subject (2). More specifically, the radio-opaque inner shaft (50b) is properly aligned with the pre-identified target (3) when the radio-opaque inner shaft (50b) is parallel to the incident angle (5) of the X-ray beam (1) and the target site (3) of the patient, as shown in FIG. 7. Conversely, FIG. 8 shows a misaligned device, whereby the needle path is not aligned with the target (3). Specifically, the radio-opaque inner shaft (50b) is not parallel to the incident angle (5) of the X-ray beam (1), and thus the needle path is not aligned with the pre-identified target (3) in the subject (2).

As shown in panel A of FIGS. 9-10 and 13 the radio-opaque inner shaft (50b, 500b, 5000b) is properly aligned with a pre-identified target in a subject when the user sees that the radio-opaque inner shaft (50b) runs through the center portion of the detachable alignment and the no portion of a vertical outer surface of the radio-opaque inner shaft (50b) is seen. As shown in panel A of FIGS. 9 and 13, proper alignment with a pre-identified target is indicated by the radio-opaque inner shaft (50b) traversing the center of a first radio-opaque alignment indicator (50c). In yet another embodiment, which is exemplified in FIG. 10, panel A, the user rotates the rotatable sphere (30) such that the radio-opaque inner shaft (50b, 5000b) is aligned with a pre-identified target in a subject by aligning a first radio-opaque alignment indicator (500c) and second radio-opaque alignment indicator (500g) to be vertically coincident. In yet another embodiment, proper alignment with a pre-identified target is indicated by the radio-opaque inner shaft (500b) traversing the center of each of the first radio-opaque alignment indicator (500c) and second radio-opaque alignment indicator (500g).

FIG. 7 and panel A of FIGS. 9, 10 and 13 show examples of when the needle path is properly aligned with the pre-identified target (3) in a subject (2). More specifically, the needle path of a fluoroscopic needle guide (1000) of the present disclosure is properly aligned when the first radio-opaque alignment indicator (50c, 500c) and the radio-opaque inner shaft (50b, 500b) are aligned parallel to the incident angle (5) of the X-ray beam (1) and the target site (3) such that the radio-opaque inner shaft (50b) appears in the center of the first radio-opaque alignment indicator (50c) and no portion of the vertical outer surface of the radio-opaque inner shaft (50b, 500b) can be seen by the user. In another embodiment [not shown], the device shown in FIG. 6, panel B, is properly aligned when the proximal ring shaped radio-opaque alignment indicator (5000c) surrounding the outermost surface of the radio-lucent of the proximal portion of the detachable alignment indicator (5000) is aligned central to the proximal ring shaped radio-opaque alignment indicator (5000c).

As shown in panel B of FIGS. 9, 10 and 13, a portion of a vertical outer surface of the radio-opaque inner shaft (50b) is visible. Hence, the needle path, as defined by the trajectory radio-opaque inner shaft (50b) is misaligned. Panel B of FIGS. 9, 10 and 13 further depicts the misalignment between the first radio-opaque alignment indicator (50c, 500c) and the radio-opaque inner shaft (50b, 500b) (e.g., off center location of the radio-opaque inner shaft). In one embodiment, the first radio-opaque alignment indicator (50c, 500c) and the second radio-opaque alignment indicator (50g, 500g) are seen by the user in positions that are not vertically coincident (e.g., different locations), and thus are misaligned with the pre-identified target (3).

When the user determines that the radio-opaque inner shaft (50b, 500b) is properly aligned with the pre-identified target in the subject (3) the user can then secure the rotatable ball (30) by tightening the detachable threaded ring (40) thereby preventing the rotatable ball (30) from unwanted rotation, which may result in misalignment with the target. Tightening of the detachable threaded ring (40) also maintains a properly aligned needle path along at least one plane.

A user can then remove detachable alignment indicator (50, 500, 5000) and insert a medical device (e.g., needle) into the hollow guide channel of the rotatable ball (30b), through the opening (30c) in the bottommost surface of the rotatable sphere, and into the patient (2) to reach the pre-identified target site (3).

In certain embodiments, in accordance with the foregoing methods, the user may change the angle of the fluoroscope (i.e., X-ray beams) during a procedure to take additional X-ray images in an alternative plane, e.g., X, Y, Z, to further determine whether the needle path is properly aligned with a pre-identified target site in a subject (3) in other planes. However, once the rotatable ball (30) is tightly secured after alignment in a first plane, then no further adjustment to the needle path within the first plane will be required when additional planes are analyzed and aligned by the user, which results in less radiation exposure to the subject and user.

When the medical procedure, veterinary procedure, or research protocol is complete, the user can then remove fluoroscopic needle guide device from the surface of the subject.

The foregoing devices, methods and embodiments thereof are merely illustrative. It will be evident to one of skill in the art that certain modifications or alternatives may be made to the foregoing exemplary embodiments without departing from the disclosure.

What is claimed is:

1. A fluoroscopic needle guide device comprising:
   an adhesive layer;
   a base member on said adhesive layer, comprising an upper portion, wherein said upper portion includes a threaded portion surrounding an opening in said base member;
   a rotatable sphere located on said opening in said base member, wherein said rotatable sphere comprises:
      a top portion having a tapered recess, wherein sidewalls of said tapered recess are smooth;
      a bottom portion having an opening; and
      a guide channel connecting said tapered recess to said opening in the bottom portion of said rotatable sphere;
   a detachable threaded ring overlying said top portion of said rotatable sphere, wherein said detachable threaded ring comprises a threaded innermost surface and a horizontal topmost surface having an opening, wherein said threaded innermost surface interlocks with said threaded portion of said base member, and innermost sidewalls of said opening that are in direct physical contact with an outer surface of said rotatable sphere, and
   a detachable alignment indicator comprising a proximal radio-opaque alignment indicator connected to a circular opening by a radio-opaque inner shaft having a cone-shaped distal portion, wherein the cone-shaped distal portion comprises smooth sidewalls, wherein said radio-opaque inner shaft passes through an opening in a bottommost surface of the cone-shaped distal portion of the detachable alignment indicator and traverses said guide channel of said rotatable sphere when the cone-shaped distal portion of the radio-opaque inner shaft is seated in said tapered recess of the rotatable sphere.

2. The fluoroscopic needle guide device of claim 1, wherein said proximal radio-opaque alignment indicator comprises a ring.

3. The fluoroscopic needle guide device of claim 2, wherein said ring of said proximal radio-opaque alignment indicator surrounds an entire outermost surface of a radiolucent portion of a proximal portion of the detachable alignment indicator.

4. The fluoroscopic needle guide device of claim 1, wherein said proximal radio-opaque alignment indicator comprises a metal.

5. The fluoroscopic needle guide device of claim 1, wherein said base member comprises a dome shaped upper portion.

6. The fluoroscopic needle guide device of claim 1, wherein said opening in said base member is a circular or spherical opening.

7. The fluoroscopic needle guide device of claim 1, wherein said opening in the bottommost surface of the detachable alignment indicator allows a needle to exit the bottommost surface of the detachable alignment indicator and pass into said hollow guide channel of said rotatable sphere.

8. The fluoroscopic needle guide device of claim 1, wherein said opening in the bottommost surface of the detachable alignment indicator allows a portion of the radio-opaque inner shaft to exit the bottommost surface of the detachable alignment indicator and pass into said guide channel of said rotatable sphere.

9. A method of using a fluoroscopic needle guide device comprising:
providing a base member and an adhesive layer, wherein said base member comprises an upper portion, and wherein said upper portion has a threaded portion surrounding an opening in said base member;
contacting said adhesive layer to a bottommost surface of said base member and contacting an opposing surface of said adhesive layer to a subject;
inserting a rotatable sphere comprising a top portion having a tapered recess and a bottom portion having an opening, into said opening in said base member, wherein the tapered recess comprises smooth sidewalk;
affixing a detachable threaded ring comprising a threaded innermost surface and a horizontal topmost surface having an opening to said threaded portion of said base member;
seating a detachable alignment indicator on said tapered recess of said rotatable sphere, wherein said detachable alignment indicator comprises a radio-opaque inner shaft having a cone-shaped distal portion comprising smooth sidewalls, and a first radio-opaque alignment indicator located at a proximal end of said detachable alignment indicator;
rotating the rotatable sphere within said opening in said base member using said detachable alignment indicator to align said first radio-opaque alignment indicator and said radio-opaque inner shaft with a pre-identified target in said subject such that said first radio-opaque alignment indicator and said radio-opaque inner shaft are aligned parallel relative to an incident angle of an X-ray beam; and
tightening said detachable threaded ring to prevent further rotation of said rotatable sphere.

10. The method of claim 9, further comprising, after said tightening step, removing said detachable alignment indicator from said rotatable sphere.

11. The method of claim 10, further comprising inserting a needle into said opening in said rotatable sphere.

12. The method of claim 9, wherein said detachable alignment indicator further comprises a second radio-opaque alignment indicator located at a distal end of said detachable alignment indicator, and wherein said second radio-opaque alignment indicator is vertically coincident with said first radio-opaque alignment indicator.

13. The method of claim 12, wherein said first radio-opaque alignment indicator, said second radio-opaque alignment indicator, said radio-opaque inner shaft; and said pre-identified target in said subject are aligned parallel relative to an incident angle of an X-ray beam.

14. The method of claim 9, wherein a topmost surface of said rotatable sphere is located above a topmost surface of said upper portion of said base member and a bottommost surface of said rotatable sphere is located above a bottommost surface of said base member.

15. The method of claim 9, wherein an outer surface of said rotatable sphere is in direct contact with an inner surface of said opening in said detachable threaded ring and an inner surface of said opening in said base member.

* * * * *